(12) United States Patent
Huang et al.

(10) Patent No.: US 6,733,475 B2
(45) Date of Patent: May 11, 2004

(54) SAFETY SYRINGE OF EASY TO PULL OUT THE PLUNGER

(75) Inventors: Chin-Shu Huang, Hsinchu (TW); Tzu-Sheng Fan, Miao Li Hsien (TW); Chien-Wei Chung, Taichung (TW)

(73) Assignee: Taiject Medical Device Co., Ltd., Miaoli (TW)

( * ) Notice: Subject to any disclaimer, the term of this patent is extended or adjusted under 35 U.S.C. 154(b) by 104 days.

(21) Appl. No.: 10/141,137

(22) Filed: May 9, 2002

(65) Prior Publication Data

US 2003/0153877 A1 Aug. 14, 2003

(30) Foreign Application Priority Data

Feb. 8, 2002 (TW) ...................................... 91201649 U

(51) Int. Cl.⁷ ................................................ A61M 5/00
(52) U.S. Cl. ........................ 604/110; 604/198; 604/218; 604/228; 128/919
(58) Field of Search ................................ 604/110, 181, 604/192, 197, 198, 218, 228, 232, 240–243, 263; 128/919; 222/386, 390

(56) References Cited

U.S. PATENT DOCUMENTS

| 4,747,830 A | * | 5/1988 | Gloyer et al. | ................ | 604/110 |
| 5,242,400 A | * | 9/1993 | Blake et al. | ................ | 604/110 |
| 5,242,419 A | * | 9/1993 | Kiner et al. | ................ | 604/195 |
| 5,308,329 A | * | 5/1994 | Mazur et al. | ................ | 604/110 |
| 5,536,253 A | * | 7/1996 | Haber et al. | ................ | 604/110 |

* cited by examiner

Primary Examiner—Brian L. Casler
Assistant Examiner—Cris L. Rodriguez
(74) Attorney, Agent, or Firm—Browdy and Neimark, P.L.L.C.

(57) ABSTRACT

A safety syringe comprises a barrel having a projection in a rear end thereof, a needle holder for mount of a needle, the needle holder having a dragged portion, a stopper movable in the barrel, the stopper having a drag portion adapted for engaging into the dragged portion of the needle holder and a plunger connector, a plunger for moving the stopper in the barrel having a stopper connector engaged with the plunger connector of the stopper. When pulled backwards to the end after injection, the plunger connector of the stopper is forced onto the projection of the barrel and disengaged from the plunger, enabling the plunger to be removed from said barrel.

9 Claims, 5 Drawing Sheets

SAFETY SYRINGE OF EASY TO PULL OUT THE PLUNGER

FIELD OF THE INVENTION

The present invention relates to hypodermic syringes, and more particularly to a safety syringe, which enables the plunger to be easily separated from the stopper after injection.

BACKGROUND OF THE INVENTION

In a safety syringe, the plunger has a front end terminating in a stopper, which has an arrowhead-like front tip adapted for hooking in the needle holder, for enabling the needle holder and the needle to be pulled backwards with the plunger and received inside the barrel after injection.

However, it is difficult to separate the plunger from the barrel after the needle holder and the needle have been received inside the barrel. When separating the plunger from the barrel after injection, the user has to break the plunger.

SUMMARY OF THE INVENTION

The present invention has been accomplished to provide a safety syringe, which eliminate the aforesaid drawback.

It is one object of the present invention to provide a safety syringe, which enables the plunger to be conveniently separated from the barrel after the service of the safety syringe.

It is another object of the present invention to provide a safety syringe, which is practical in use.

To achieve these objects of the present invention, the safety syringe comprises a barrel having a projection in a rear end thereof, a needle holder for holding a needle in a front end of the barrel, the needle holder having a dragged portion, a stopper movable in the barrel, the stopper having a drag portion adapted for engaging into the dragged portion of the needle holder and a plunger connector, and a plunger for moving the stopper in the barrel having a stopper connector engaged into the plunger connector of the stopper. When pulled backwards to the end after injection, the plunger connector of the stopper is forced onto the projection of the barrel and disengaged from the plunger, enabling the plunger to be removed from barrel.

DETAILED DESCRIPTION OF THE INVENTION

Figure 1:
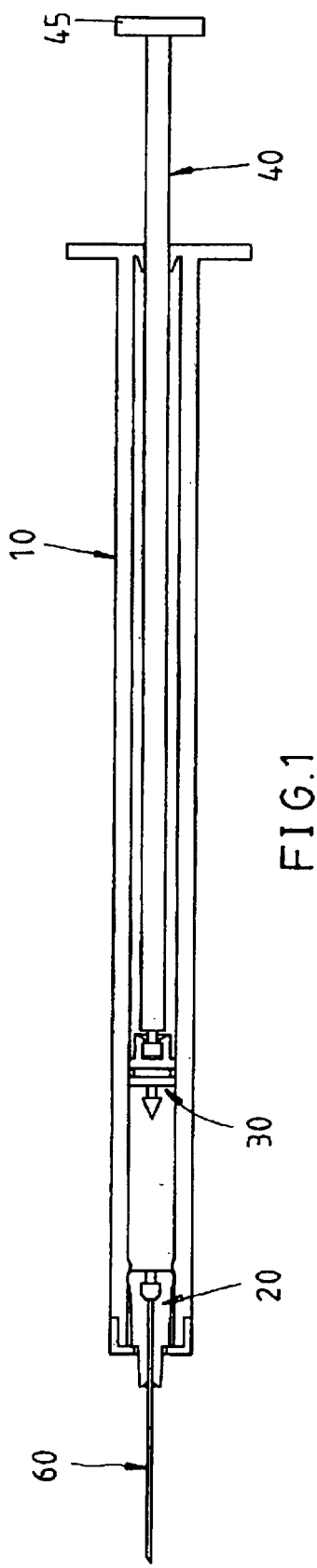
FIG. 1 is a side sectional view of the safety syringe according to a prefer embodiment of the present invention.
Figure 2:
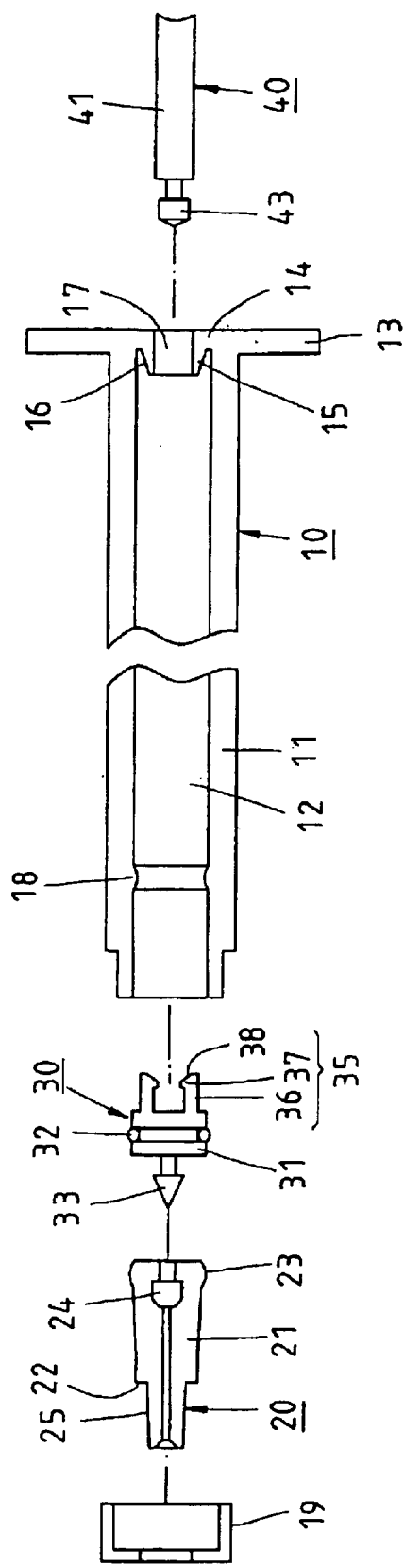
FIG. 2 is an exploded view of the safety syringe shown in FIG. 1.
Figure 3:
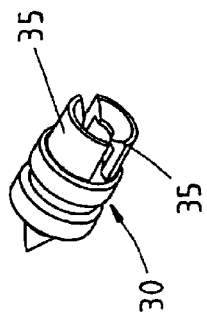
FIG. 3 is a perspective view of the stopper according to the prefer embodiment of the present invention.

Referring to FIGS. 1–3, a safety syringe is shown, which is to mount a needle 60, comprises:

A barrel 10 have a tubular body 11, a receiving hole 12 defined in the tubular body 11, a hold portion 13 provided at one end, namely, the rear end of the tubular body 11, a base flange 14 extended around at the rear end of the tubular body 11, a projection 15 of conical shape axially forwardly extended from the base flange 14 and suspended inside the tubular body 11, a sliding face 16 slopingly formed in the periphery of the projection 15, an insertion hole 17 axially extended through the center of the projection 15, a position ring 18 extended around in the inside wall of the receiving hole 12 near the other end, namely the front end, and a front cap 19 capped on the front end of the tubular body 11.

A needle holder 20 having a holder body 21 is mounted in the receiving hole 12 of the barrel 10, a stop portion 22 stopped against the tubular body 11, a seal ring 23 mounted around the periphery to seal the receiving hole 12 of the barrel 10, a dragged portion 24 in the rear end, and a needle receiving portion 25 at the front end.

A stopper 30 have a stopper body 31, a seal ring 32 extended around the periphery of the stopper body 31 and disposed in close contact with the peripheral wall of the receiving hole 12 of the barrel 10, a drag portion 33 for engaging with the dragged portion 24 of the needle holder 20, and a plunger connector 35 backwards extended from the rear side of the stopper body 31. Two hook plates 36 symmetrically disposed at two sides of the plunger connector 35. Each hook plate 36 has a hook 37 and formed a tapered sliding face 38 at the front side thereon.

A plunger 40 is a rod member having a shank 41 insertable into the insertion hole 17 and the receiving hole 12 of the barrel 10, a push-pull portion 45 disposed at one end, namely, the rear end of the shank 41, and a stopper connector 43 forwardly extended from the other end, namely, the front end of the shank 41.

When assembled, as shown in FIG. 1, the stopper connector 43 of the plunger 40 is engaged into the plunger connector 35 of the stopper 30.

Figure 4:
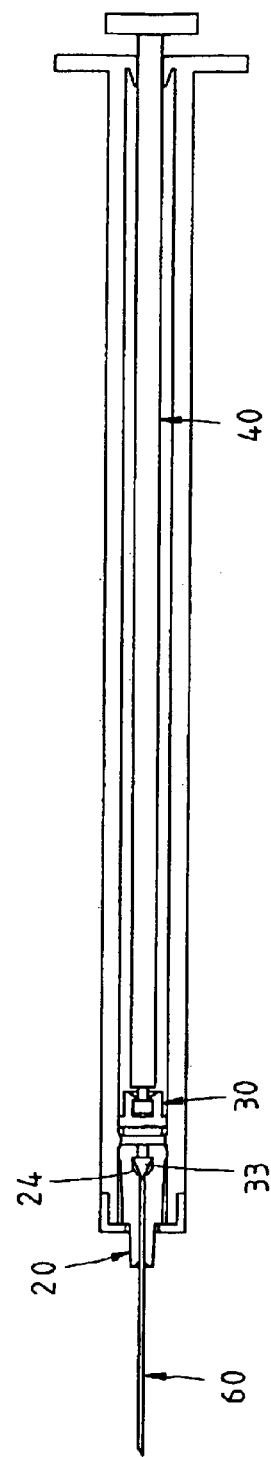
FIG. 4 is a side sectional view of the prefer embodiment of the present invention, showing the stopper engaged into the needle holder.

During injection, the stopper 30 is moved with the plunger 40 toward the front end of the barrel 10 to force medicine out of the needle holder 20 and the needle 60. As show in FIG. 4, after injection, the drag portion 33 of the stopper 30 is forced into engagement with the dragged portion 24 of the needle holder 20.

Figure 5:
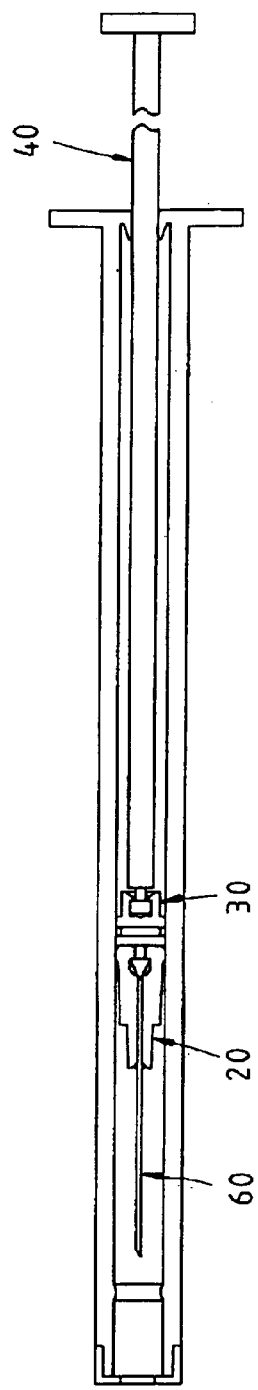
FIG. 5 is a side sectional view of the prefer embodiment of the present invention, showing the needle holder and the needle dragged backwards.

Referring to FIG. 5, when pulling the plunger 40 backwards after injection, the needle holder 20 and the needle 60 are moved with the stopper 30 and the plunger 40 backwards into the inside of the receiving hole 12 of the barrel 10.

Figure 6:
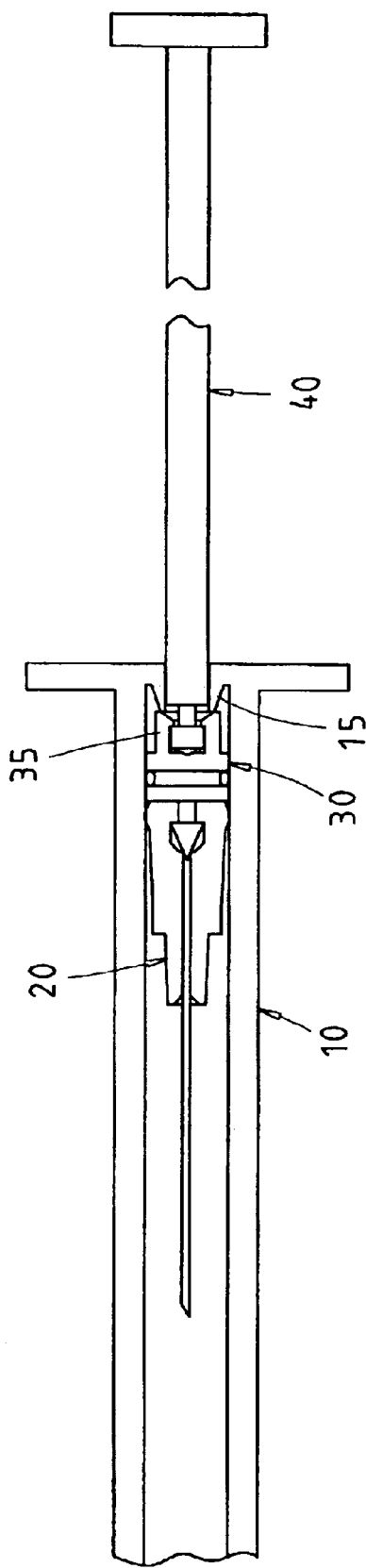
FIG. 6 is a side sectional view of the prefer embodiment of the present invention, showing the stopper moved to the projection of the barrel.
Figure 7:
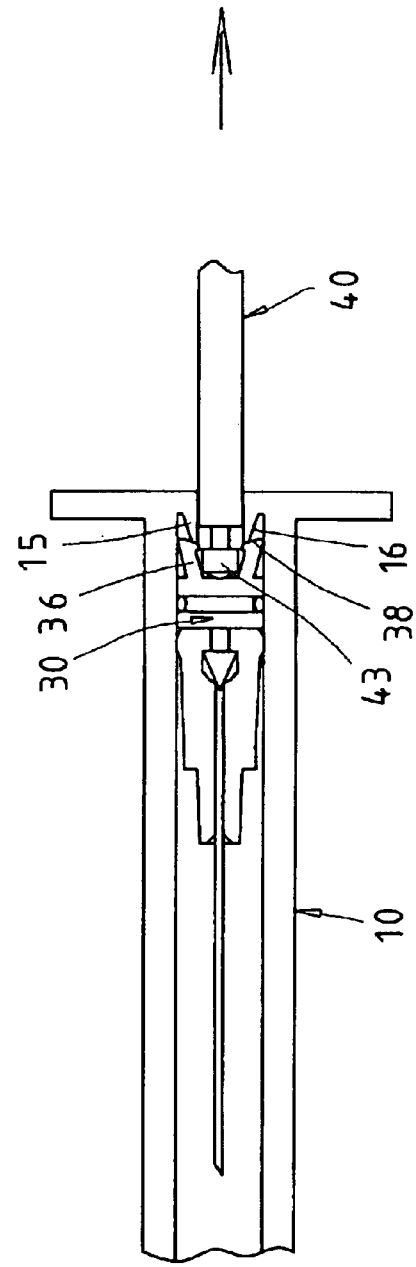
FIG. 7 is a schematic view of the prefer embodiment of the present invention, showing the plunger connector of the stopper forced onto the projection of the barrel and expanded.

Referring to FIGS. 6 and 7, when pulled the plunger 40 backwards to the end, the tapered sliding faces 38 of the hook plates 36 of the plunger connector 35 are forced radially outwards by the sloping sliding face 16 to expand the hook plates 36, thereby causing the plunger connector 35 to be disengaged from the stopper connector 43 of the plunger 40.

Figure 8:
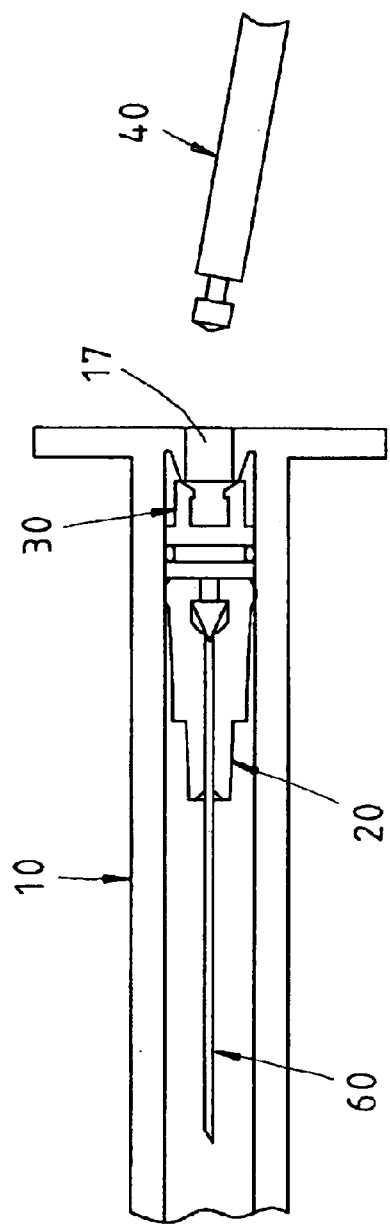
FIG. 8 is a side sectional view of the prefer embodiment of the present invention, showing the plunger is pulled out.

As show in FIG. 8, At this time, the user can easily remove the plunger 40 from the barrel 10, remaining the stopper 30, the needle holder 20, and the needle 60 inside the barrel 10.

Figure 9:
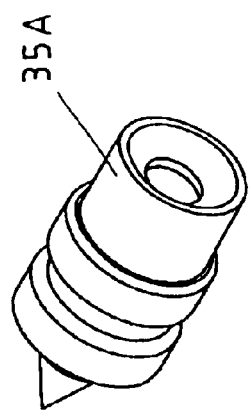
FIG. 9 is an elevational view of an alternate form of the stopper according to the present invention.

FIG. 9 shows an alternate form of the plunger connector 35A of the stopper, has a cylindrical shape.

Figure 10:
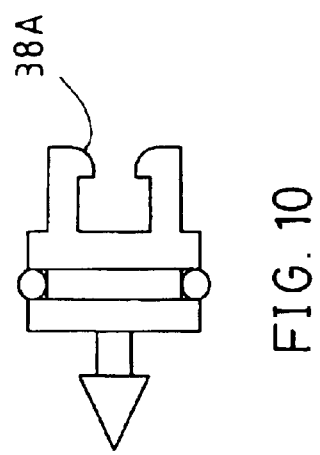
FIG. 10 is a plain view of another alternate form of the stopper for the safety syringe according to the present invention.

FIG. 10 shows another alternate form of the sliding face 38A of the stopper. According to this alternate form, the sliding face 38A of each hook plate of the stopper is smoothly arched.

Figure 11A:
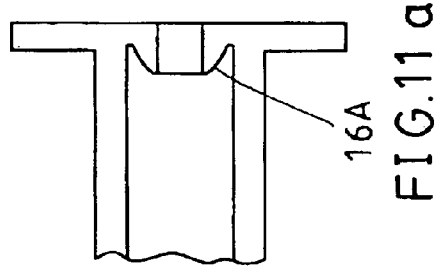
FIG. 11a and FIG. 11b is a plain view of two alternate forms of the projection of the barrel according to the present invention.

FIG. 11a shows another alternate form of the sliding face 16A of the projection of the barrel curved outwards.

Figure 11B:
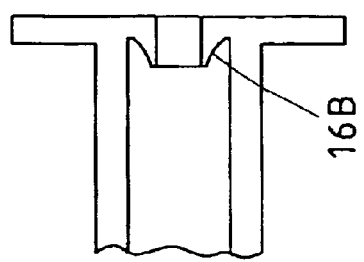

FIG. 11b shows still another alternate form of the sliding face 16B of the projection of the barrel curved inwards.

Figure 12:
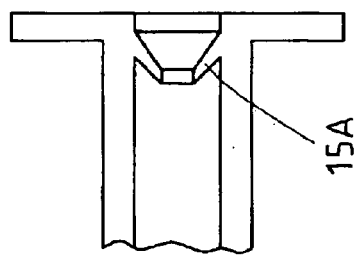
FIG. 12 is a plain view of an another alternate form of the projection of the barrel according to the present invention.

FIG. 12 shows the projection 15A formed integral with the peripheral wall of the receiving hole 12 of the barrel 10.

As indicated above, the safety syringe of the present invention achieves the following advantages:

1. When pulled the needle holder and the needle backwards to the inside of the barrel, the plunger can easily be separated from the stopper and removed from the barrel.
2. The structure of the safety syringe is simple, and no any additional means is needed to separate the plunger from the stopper after the needle holder and the needle have been pulled backwards to the inside of the barrel.

What the invention claimed is:

1. A safety syringe, which is to mount a needle, comprising:
    a barrel having a tubular body defining a receiving hole, a projection disposed in one end of said tubular body, and an insertion hole axially extended through said projection;
    a needle holder mounted in the receiving hole of said barrel and for holding the needle outside said tubular body of said barrel, said needle holder having a dragged portion;
    a stopper mounted in said receiving hole of said barrel for axial movement between two ends of said barrel, said stopper having a drag portion adapted for engaging into the dragged portion of said needle holder for enabling said needle holder to be moved backwards with said stopper in said barrel, and a plunger connector; and
    a plunger inserted into the insertion hole of said barrel, said plunger having a stopper connector engaged into the plunger connector of said stopper for enabling said stopper to be moved with said plunger;
    wherein when pulled said plunger backwards to carry said stopper, said needle holder and said needle backwards on end of said barrel, said plunger connector of said stopper is forced by the projection of said barrel to expand, thereby causing said stopper to be disengaged from said plunger for enabling said plunger to be removed from said barrel.

2. The safety syringe as defined in claim 1, wherein said plunger connector of said stopper have two hook plates symmetrically disposed at two sides.

3. The safety syringe as defined in claim 1, wherein said plunger connector of said stopper has a cylindrical shape.

4. The safety syringe as defined in claim 1, wherein said projection of said barrel has a conical shape.

5. The safety syringe as defined in claim 4, wherein said projection of said barrel has a sliding face formed in the periphery thereof.

6. The safety syringe as defined in claim 1, wherein said sliding face of the projection of the barrel is a curved surface.

7. The safety syringe as defined in claim 1, wherein said plunger connector of said stopper has a sliding face open outwards and adapted for guiding said plunger connector onto the projection of said barrel.

8. The safety syringe as defined in claim 7, wherein the sliding face of said plunger connector of said stopper is slopes linearly.

9. The safety syringe as defined in claim 7, wherein the sliding face of said plunger connector of said stopper is smoothly arched.

* * * * *